US005833945A

United States Patent [19]
Sakuma

[11] Patent Number: 5,833,945
[45] Date of Patent: Nov. 10, 1998

[54] ANIMAL MODEL OF PATHOLOGICAL BEHAVIOR

[76] Inventor: Moto Sakuma, 4434 Grayton, Detroit, Mich. 48224

[21] Appl. No.: 928,151

[22] Filed: Sep. 12, 1997

Related U.S. Application Data

[63] Continuation of Ser. No. 789,819, Jan. 27, 1997, which is a continuation of Ser. No. 650,555, May 20, 1996, which is a continuation of Ser. No. 467,764, Jun. 6, 1995, which is a continuation of Ser. No. 253,422, Jun. 2, 1994, which is a continuation of Ser. No. 954,016, Sep. 30, 1992.

[51] Int. Cl.$^6$ ............................ A61K 49/00; A01K 29/00
[52] U.S. Cl. ...................... 424/9.1; 119/174; 800/DIG. 4
[58] Field of Search .................................. 800/2, DIG. 4; 424/9.1; 119/174

[56] References Cited

U.S. PATENT DOCUMENTS

4,736,866    4/1988    Leder et al. ................................. 800/2

OTHER PUBLICATIONS

R Arevalo et al (1991) Life Sci 49:53–66 (Abstract).
L Allikmets (1975) Sint. Izuch. Fiziol. Akt. Veshchestv, Tezisy Dolcl. Mezhvuz Nauchn. Konf. Uchastieun, 1975, 7–11 (Abstract).
KM Kantak et al (1980) Pharmacol. Biochem Behav 12:173–9.
MD Tricklebank et al (1978) Pharmacol. Biochem. Behav 9:181–189.
Archer, J., "Tests for Emotionality in Rats and Mice: A Review", *Anim. Behav.* 21:205–235 (1973).
Bogdanski, D.F. et al., "Pharmacological Studies with the Serotonin Precursor, 5–Hydroxytryptophan", *J. Pharmacol Exper. Therapeut.* 122:182–194 (1958).
Broadhurst, P.L., "Psychogenetics of Emotionality in the Rat", *N.Y. Acad. Sci. Ann.* 159:806–824 (1969).
Broadhurst, P.L., "Maternal Effects in the Inheritance of Behavior", *Animal Behav.* IX, 3–4:131–141 (1960).
Broadhurst, P.L., "The Maudsley Reactive and Nonreactive Strains of Rats: A Survey", *Behavior Genet.* 5:299–318 (1975).
Falconer, D.S., "Selection of Mice for Growth on High and Low Planes of Nutrition", *Genetic Res.* 1:91–113 (1960).
Fog, R., "Rage Reactons Produced in Rats By a Combnation of Thymo–Leptics and Monoamine Oxidase Inhibitors", *Pharmacol. Res. Commun.* 1:76–83 (1969).
Fuller, J.L. et al,. *Foundation of Behavioral Genetics* (The C.V. Mosbly Co., St. Louis, MO) pp. 17–20, 32–39, 50–73, 77–93, 99–111, 155–179, 475–515 (1978).
Furchtgott, E. et al., "Activity and Emotionality in Pre–and Neonatally X–Irradiated Rats", *J. Comp. Physiol. Psychol.* 51:541–545 (1958).
Gottlieb, J.S. et al., "The Effect of Antimetabolics on Embryonic Development", *JMSMS* 57:364–366 (1958).
Hall, C.S., "The Inheritance of Emotionality", *Sigma XI Quartlery* 26:16–27, 37 (1938).
Hall, C.S., "Defecation and Urination as Measures of Individual Differences in Emotionality", *J. Comp. Psychol.* 18:385–403 (1934).
Hockman, C.H., *J. Comp. Physiol. Psychol.* 54(6):679–684 (1961).
Ladias, J.A. et al., "A New Apolipoprotein B–100 Variant in a Family With Premature Atherosclerosis and Hyerapobetalipoproteinemia", *JAMA* 262:1980–188 (1989).
Lewis, A.J. et al., "Determination of the Optimum Dietary Proportions of Lysine and Tryptophan For Growing Rats Based on Growth, Food Intake, and Plasma Metabolites", *J. Nutrition* 107:1361–1368 (1977).
Mayeno, A.N. et al., "Characterization of 'Peack E,' a Novel Amino Acid Associated with Eosinophilia — Myalgia Syndrome", *Science* 250:1707–1708 (1990).
MMWR, "Analysis of L–Tryptophan For The Etiology of Eosinophilia — Myalgia Syndrome" 39:587–591 (1990).
Pare, W.P. "Relationship of Varous Behaviors in the Open–field Test of Emotionality", *Psycholol. Reports* 14:19–22 (1964).
Pike, R.L., "congenital Cataract in Albino Rats Fed Defferent Amounts of Tryptophan and Niacin", *J. of Nutrition* 44:191–204 (1951).
Pond, W.G. et al., "Effects of The α–Keto Analogue ot Tryptophans and The Level of the Corresponding Amno Acids on Growth of Rats", *J. Nutrition* 83:85–93 (1964).
Randrup, A. et al., "Dopa and Other Naturally Occurring Substances as Causes of Stereoptypy and Rage in Rats", *Acta Psychiat. Scand Suppl.* 191(42):193–199 (1966).
Reuter, "Better Diet May Help Asian Kids Grow Bigger in U.S.," *The Detroit News*, Feb. 19,1992.
Sakimoto, K., "The Cause Of The Eosinophilia — Myalgia Syndrome Associated With Tryptophan Use" *New Engl. J. Med.* 323:992–993 (1990).
Sakuma, M. Soc. *Neuroscience*, "A Study of the Adverse Effects of 5–HT Precursor–Treatments Related to EMS", Abstract (1992).
Sakuma, M. et al., "Effects of Prenatal Tryptophan Diets on Behavior in Mature Rats", Federation Proceedings, Abstract, vol. 43:1974 (1984).

(List continued on next page.)

*Primary Examiner*—Bruce R. Campell
*Attorney, Agent, or Firm*—Harness, Dickey & Pierce, P.L.C.

[57] ABSTRACT

The present invention provides a phenotypically stable altered animal which exhibits unprovoked rage reaction indicative of high emotionality, stereotyped behavior and is useful as a model of psychotic behavior. The animals of this invention ($F_2$) were obtained by inbreeding mature offspring ($F_1$) of rats whose mothers received high tryptophan diets during their third trimester of gestation. There is also an increased body weight which evidences physical alteration. The present invention also relates to the preparation and use of animal models for the study of psychosis, pathological psychotic behavior in humans and the effects of tryptophan in successive generations. The prenatal effects of tryptophan on later generations can also be used to increase the body weight of experimental animals and livestock.

1 Claim, No Drawings

OTHER PUBLICATIONS

Sudak, H.S. et al., "Behavioral — Neurochemical Correlation in Reactive and Nonreactive Strains of Rats", *Science* 146:418–420 (1964).

Thompson, W.R. "Influence Of Prenatal Maternal Anxiety On Emotionality In Young Rats" *Science* 125:698–699 (1957).

Vincent, N.M. "The Effects Of Prenatal Alcoholism Upon Motivation, Emotionality, and Learning In The Rat" *Amer. Psychologist* 13:401 (1958).

Warkany, J. et al., "Congenital Malformations Induced in Rats by Maternal Nutritional Defiency", *Society for Experimental biology and Medicine,* Abstract, 54:92–94, 14317P (1943).

Warkany, J. et al., "Congenital Malformations Induced in Rats by Maternal Riboflavin Defiency: Dentofacial Changes", *J. Amer. Dental Assoc.* 51:139–154 (1955).

Werboff, J. et al., "Behavioral Effects of Prenatal Drug Administration in the White Rat" *Pediatrics* 27:318–324 (1961).

Werboff, J. et al., "Postnatal Effect of Antidepressent Drugs Administered During Gestation", *Exp. Neur.* 3:542–555 (1961).

Curtis, P.B. et al., "The Nutritive Value of Certain Animal Protein Concentrates", *J. of Nutr.* 5:503–517 (1932).

Fernstrom, J.D. et al., "Effects of Skim Milk, Whole Milk and Light Cream on Serum Tryptophan Binding and Brain Trytophan Concentrations in Rats", *J. of Nutr.* 105:1359–1362 (1975).

Khorasanizadeh, S. et al., "Folding and Stability of a Tryptophan–Containing Mutant of Ubiquitin", *Biochem.* 32:7054–7063 (1993).

Ladokhin, A.S. et al., "Flourescence Study of a Mutant Cytochrome $b_5$ with a Single Tryptophan in the Membrane–Binding Domain" *Biochem.* 30:10200–10206 (1991).

Lauder and Krebs, "Serotonin as a Differentiation Signal in Early Neurogenesis", *Dev. Neurosci.* 1:15–30 (1978).

"Nerve Cells and Electric Properties of Cell Membranes", *Molecular Cell Biology* (Scientific American Biology) pp. 786–788, 798–799 (1990).

"Serotonin — New Vistas — Biochemistry and Behaviorial and Clinical Studies", *Advances in Biochemical Psychopharmocology* (Raven Press, New York) pp. 133–142 (1974).

Yehuda, S. et al., "Increased Serotonin Level Via Augmented Tryptophan Diet and Its Effects on Escape Learning", *Inter. J. Neuroscience* 15:193–196 (1981).

I Lieblich et al (1980) Brain Research 185:253–264.

DV Coscina et al (1973) Pharm Biochem Behav 1:1–6.

ANIMAL MODEL OF PATHOLOGICAL BEHAVIOR

This is a continuation of U.S. patent application Ser. No. 08/789,819, filed Jan. 27, 1997 (abandoned), which is a continuation of U.S. patent application Ser. No. 08/650,555, filed May 20,1996 (abandoned), which is a continuation of U.S. patent application Ser. No. 08/467,764, filed Jun. 6, 1995 (abandoned), which is a continuation of U.S. patent application Ser. No. 08/253,422, filed Jun. 2, 1994 (abandoned), which is a continuation of U.S. patent application Ser. No. 07/954,016, filed Sep. 30, 1992 (abandoned).

FIELD OF THE INVENTION

The present invention relates generally to animal models of pathological behavior and, more particularly, to a phenotypically altered animal. Specifically, this invention relates to an animal, bred from the $F_1$ offspring of prenatally tryptophan-dieted rats, with behavioral characteristics resembling psychosis in humans.

BACKGROUND OF INVENTION

Psychosis is a general term used to describe mental illness which results in the severe disturbance of brain function, including emotion and intellectuality. The study of psychosis and its underlying causes and treatments are thus essential to society.

Animals exhibit various behavioral characteristics which researchers have used to select animal models for study. As an example, emotional instability is associated with psychosis; thus behavior indicative of this characteristic has been used as a criterion for selecting appropriate animal models. For example, in his review of articles on emotional stability, Archer, J., Anim. Behav. 21:205–35 (1973) concluded that low emotionality in rats accelerated more exploration (rearing) and high emotion inhibited exploration. Additionally, Broadhurst, P. L., Behav. Genetics, 5(4):299–319 (1975) and Hall, C. S. J. Comp. Psychol. 18:385–403 (1934) indicated that an increase in defecation in animals can constitute an emotional response. However, Archer, supra, noted that defecation decreases to normal levels in repeated testing and recommended that other behavioral data be considered before concluding emotionality is present.

Another characteristic associated with pathological behavior useful for model selection is stereotyped behavior. Stereotypy is generally defined as senseless movements, actions, and/or words. Hall, C. S. Sigma XJ Quarterly 17–37 (1938) defined stereotypy as behavior characterized by the persistence of the same response in a free-choice situation and by a difference in the pattern of movement between an emotionally stable and unstable animal. For example, Munkvad, Acta Psycht. Scand. 191:193–199 (1966) described sniffing, licking and repetitive cage biting as stereotypy exhibited by rats treated with monoamine oxidase inhibitor (MAOI) and then injected with 5HTP (a serotonin precursor). Unprovoked outbursts of violence, fast movement, and vocalization are also behavioral characteristics associated with psychosis which can be used for model selection. Generally, researchers classify this data under "rage reaction." See, Randrup, A. et al., Acta Psychiat Scand. SuppL 191(42):193–199 (1966).

In selecting appropriate animal models, it was once thought that abnormal behavior could be a consequence of parental care as opposed to an internal change, thus studies required cross-fostering as a control. However, cross-fostering experiments testing this hypothesis failed to show a difference in activity in the stressed and nonstressed offspring raised by their own mother. Hockman, C. H., J. Comp. Physiol. Psychol. 54(6) 679–684 (1961). These results suggested reactions caused by postnatal separation experience (i.e. cross-fostering) as opposed to postnatal care.

A common model of pathological psychotic behavior is drug-induced psychotic disturbance. However, the use of such models requires the Injection of drugs, such as amphetamines or morphine, to obtain the desired behavior. Moreover, drug-induced models are not entirely satisfactory for the desired psychotic disturbance due to the extremity of behaviors resulting from drug manipulation. For instance, in cats, a ten-fold higher dose of amphetamine is required to induce stereotyped behavior, than is required to awaken the cat. The high dosage required for drug-induced behavior also usually results in neurotoxicity which is undesirable in a model of psychosis. Moreover, drug manipulation may produce unavoidable stimulational effects on the animal due to the injection technique utilized (e.g. cutaneous, peritoneal, or intraventricular injection).

Prenatal stimulation to change the uterine environment has been used to induce abnormalities (and thus possible models of psychosis) in offspring. For example, to add stress to the uterine environment during gestation, Fuchtgoh, E. et al., J. Comp. Physiol. Psychol. 51:541–545 (1958) applied x-irradiation, Thompson, W. R. Science 25:698–699 (1957) applied shock treatments, and Vincent, N. M. Am. Psychol. 13:401 (1958) administered alcohol to rats. Bogdanski, D. F. et al., J. Pharmacol. Exp. Therap. 122:182–194 (1958) also noticed that 5HTP injection into non-pregnant animals produced a marked increase in uterine serotonin levels in cats and dogs. However, these studies did not report retained heritable effects in the $F_2$ generation.

With respect to retained heritable characteristics useful for the study of pathological behavior in psychotics, one animal model, the Maudsley rat strain, has been shown to exhibit high emotion in successive generations. The Maudsley rat was established by a classic selection scheme for behavior indicating high emotion and further in-breeding. Broadhurst, supra. The ability of selection by phenotype to produce a stable and reliable strain has been confirmed by the use of the Maudsley rat strain in experiments reported in over 300 publications. It is interesting to note that the Maudsley rat has abnormally high levels of brain serotonin, see Sudak, H.S . et al., Science 146:418–420 (1964). The genetic basis of the origin of the Maudsley rat has not, however, yet been defined.

Sakuma, M., et al., Abstract No. 1974 in the 68th Federation Proceedings (1984) examined the effects of prenatal tryptophan diets on $F_1$ offspring, suggesting that behavioral changes may derive from the prenatal diet because the offspring with prenatal high tryptophan diets exhibited low activity, whereas the offspring with prenatal low tryptophan diets had high activity. However, the low and high tryptophan diet groups did not differ in any other quantifiable open field behaviors. For example, no statistically significant differences in defecation, spontaneous turning, flat walking and head shaking were observed, nor did either group display any rage reaction. Thus there was no indication that later generations would exhibit such pathological pyschotic behavior.

The effects of tryptophan are of particular interest because tryptophan is used in various clinical applications, for example, as a painkiller, sleeping pill, bed-wetting control, menstruation discomfort reliever, and a sedative for depressive anxiety. However, it appears that tryptophan is not without adverse effects. For example, Mayeno, et al. *Science* 250:1707–8 (1990) recently Identified the offender of Eosinophilia-Myalgia Syndrome (EMS), a malady associated with muscle pain, to be a combination of 1-ethyltryptophan and tryptophan. Sakuma, M., Abstract, Society for Neuroscience (1992), postulates that EMS may be caused by combined influences involving tryptophan toxicity with conditions of genetic background and/or underlying metabolic abnormality as the predisposition. Therefore, further study of the effects of tryptophan use would be desirable.

It would thus be desirable to provide an animal model for the study of pathological behavior relevant to psychotic syndromes. It would further be desirable to provide a simple method of production of such a model. It would also be desirable to have an animal model for the study of the genetic effects of tryptophan use. It would further be desirable to have a method for the breeding of heavier experimental animals and livestock.

SUMMARY OF THE INVENTION

The present invention provides an emotionally and behaviorally altered animal useful as a model of pathological behavior seen in psychosis. The animals of this invention were obtained by inbreeding mature $F_1$ offspring of rats wherein the mothers of the $F_1$ received 3% (by weight) tryptophan supplemented diets during their third trimester of gestation. The present invention also relates to the preparation and use of animal models for the study of psychosis and the effects of tryptophan on successive generations. The effects of tryptophan treatment on successive generations can also be used to increase the body weight of experimental animals and livestock.

The phenotypic attributes of these altered rats include behavior indicative of high emotionality, stereotypy and unprovoked rage reaction thus providing an appropriate congenital animal model for pathological behavior. Increased body weight of successive generations as a result of prenatal tryptophan treatment is also useful for breeding heavier laboratory animals and livestock.

DESCRIPTION OF THE PREFERRED EMBODIMENTS OF THE INVENTION

Pregnant Sprague-Dawley rats artificially inseminated with Sprague-Dawley male sperm were obtained from Zivic-Miller Laboratories Inc., Allison Park, Pa. 15101. While in their third trimester of gestation (last week), the pregnant experimental rats received Pregnant Rat Tryptophan Deficient Meal available from Bio-Serv, Inc., (Frenchtown, N.J.) a corn powder diet, supplemented with three percent (3%) by weight tryptophan. On delivery day, the rats received regular Purina Lab Chow (0.3% tryptophan). The control group was fed the corn powder diet supplemented with only 0.3% by weight tryptophan during the last trimester of pregnancy.

Although the $F_1$ progeny of the tryptophan stimulated mothers exhibited a decrease in activity, no other signs of abnormality appeared. Several of the $F_2$ generation, which was produced by inbreeding mature $F_1$ generation rats, exhibited a variety of behavioral abnormalities associated with emotionality. The precise mechanism of inheritance is not yet known. In part the mechanism of inheritance for animal behavior remains unsolved due to the complexity of gene activity on a behavior.

These altered $F_2$ rats showed less activity evaluated by low rearing counts and long stays in the corner. Also, these rats displayed a high rage reaction. Unprovoked, the rats shrieked and displayed aggressive and bizarre behavior. These rats also exhibited low activity by a short latency in corner reaching and a long latency in face washing. The body weight of these rats was also higher than that of control rats. Also, the rats showed stereotypy.

These rats' emotional status demonstrated by the low activity, stereotypy, and rage reaction are useful for the study and therapy of psychosis. To confirm inheritance of targeted behavior, the characteristics of behavior are required to possess remarkable, distinguishable and glance-recognitionable behavior with persistent and frequent appearance. Among the behaviors of the animals of the present invention, the rage reaction and open-field behavior meets these demands. Furthermore, this method's effect of causing increased body weight can be used in the preparation and use of livestock. These rats and other animals produced by prenatal dietary intake of tryptophan can also be used in the study and therapy of tryptophan induced mutations.

$F_2$ rats, exhibiting the desired phenotype may be bred, cross-bred or in-bred and their progeny selected for the desired characteristics. In the alternative, $F_2$ rats not exhibiting the desired phenotype may be bred and their offspring which exhibit the desired phenotype, if any, may be selected. In any event, once the desired phenotype is exhibited, successive generations can be obtained through natural breeding or artificial insemination and behavioral selection.

For Specific Examples 1 through 3, Sprague-Dawley rats were used. There were 31 males and 28 females in the experimental group and 8 males and 13 females in the control group. Observations were recorded at the ages of 3, 6, 8 and 10 weeks in both the $F_1$ and $F_2$ generations. The specific examples are of the $F_2$ generation of pregnant rats which received a 3% tryptophan diet in their last trimester of gestation. The parents ($F_1$) of these rats were fed a normal diet containing 0.3% tryptophan.

SPECIFIC EXAMPLE 1

Rage Reaction

In general, experimental rats, such as the Sprague-Dawley, are highly inbred, docile and easy to handle and test, especially for the animal care person. The 3% tryptophan (H group) rats, however, exhibited extremely aberrant and aggressive behavior.

One female and one male from two litters out of six litters of the H Group exhibited explosive pathological behaviors without stress or environmental change. For example, at ten weeks of age, during the open-field test, the female rat suddenly began a loud monotonous shrieking, then ran along the test box wall and jumped out from the box. Once out of the box, the female stood at the corner of the desk where the test box was placed, and continually shrieked and stared at the tester. The male rat showed even more aggressive and bizarre behaviors. For example, the male displayed abnormal characteristics by looking around as if in fear. Then, he screamed out loudly without provocation. While screaming, the rat snarled and bared his fangs at the tester. The behavior was characteristic of anger or a threat response. Finally, he rushed at his tester and leapt from the box.

Open-field behavior is clearly influenced by genes at a variety of loci; however, the $F_2$ progeny were produced by sibling mating which leads to progressive increases in homozygosity in each generation. Therefore, the $F_1$ will be backcrossed to two parent generations (B1 and B2) to determine the phenotypic variations, i.e., additive, dominance, environment and maternal components. Also, reciprocal crosses will be performed to determine maternal effects and sex linkage for confirmation.

SPECIFIC EXAMPLE 2

Stereotyped Behavior

Although the H group and the control group did not differ in the number of head shakes and body turns, the actual pattern of these behaviors did differ. Therefore, according to Hall, the rats displayed signs of stereotypy: the control group usually shook their heads side to side, whereas the H groups tossed their heads back repeatedly. The control group's body turning generally consisted of one or one and one-half turns while the H group's body would circle over three times in one spot.

SPECIFIC EXAMPLE 3

Open-Field Test Data (The data described below is in Table I which follows.)

A. Rearing (exploration; standing on rear extremities).

The 3% tryptophan group (H group) had lower scores than that of the control group (M group). So, using the Archer supra, criteria, both genders of the H group display abnormal open-field behaviors which are evaluated as high emotion.

B. The Corner Crouch
  i. The first corner reach time (seconds) was measured as the time for the rat, starting from placement in the middle of the test box, to reach the test box corner, where the rat usually sits or crouches and does grooming, face washing, and sleeping. The male rats of the H group were quicker to reach the corner than male contol rats.
  ii. The corner crouching duration is the time measured while the rats remained in the corner and did not move around. The female rats of the H group had a long corner crouching duration which indicates low activity, i.e. apparently consistent with high emotionality.

C. Face Washing
  i. The first facial wash is the time measured from placement in the middle of the test box, until the rat started the first face wash. Both male and female rats of the H group showed a delay before starting to face wash.
  ii. The facial wash counts have been reported but are combined with the grooming counts. This data is believed to show emotionality.

D. Defecation

The feces were counted for five minutes during the open field test. The females of the H group had significantly lower counts than the control group.

TABLE 1

Results of open-field test scores in $F_2$ progeny (t-test).

| | Control (M) vs. 3% TRP Group (H) | |
| --- | --- | --- |
| Activity | Male | Female |
| 1st Rearing (seconds) | ns | ns |
| Rearing Count | M > H | M > H |
| | 6 wk, p = 0.1% | 3 wk, p = 1% |
| | | 6 wk, p = 2% |
| 1st Corner Reach (seconds) | M > H | ns |
| | 6 wk, p = 1% | |
| Corner Crouch Duration (seconds) | ns | M < H |
| | | 3 wk, p = 0.1% |
| 1st Facial Wash (seconds) | M < H | M < H |
| | 3 wk, p = 1% | 3 wk, p = 5% |
| | 8 wk, p = 5% | |
| | 10 wk, p = 0.1% | |
| Facial Wash Count | ns | ns |
| Defecation (counts) | ns | M > H |
| | | 10 wk, p = 5% |

M group: 8 males and 13 females
H group: 31 males and 28 females
ns = not significant
p = probability

SPECIFIC EXAMPLE 4

Body Weight

As shown in Table 2, both genders of the H group described in previous Examples show heavier body weight than that of the control group. Thus, prenatal tryptophan dietary treatment produces good growth even in the second generation.

TABLE 2

Body Weight in Grams of $F_2$ Progeny

| | MALE | | | Female | | |
| --- | --- | --- | --- | --- | --- | --- |
| AGE | 3% TRP Group (H) | Control (M) | p | 3% TRP Group (H) | Control (M) | p |
| 3 weeks | 77.06 ± 15.7 | 68.88 ± 9.1 | | 77.86 ± 18.8 | 66.08 ± 10.3 | 5% |
| 6 weeks | 214.90 ± 44.3 | 185.50 ± 11.7 | | 181.75 ± 34.8 | 161.38 ± 11.76 | |
| 8 weeks | 344.29 ± 32.9 | 308.38 ± 17.3 | 1% | 245.64 ± 23.2 | 214.15 ± 12.5 | 0.1% |
| 10 weeks | 411.29 ± 47.7 | 383.13 ± 22.2 | | 278.54 ± 26.9 | 246.92 ± 13.5 | 0.1% |

M Group: 8 males and 13 females
H Group: 31 males and 28 females
p = probability Those skilled in the art can now appreciate from the foregoing description that the broad teachings of the present invention can be Implemented in a variety of forms. For example, other species of animals can be employed. In some circumstance, for instance, it may be desirable to use a species, e.g., a primate such as the rhesus monkey, which is evolutionarily closer to humans than rats. Moreover, although a ten-fold dietary increase in tryptophan (0.3% to 3.0% by weight) was used in the preferred embodiment described herein, the present invention includes other increased levels of tryptophan which are sufficient to produce the desired heritable phenotype without undue toxic side effects. Therefore, while this invention has been described in connection with particular examples thereof, the true scope of the invention should not be so limited since other modifications will become apparent to the skilled practitioner upon a study of the drawings, specification and following claims.

All publications cited herein are incorporated by reference.

What is claimed is:

1. A method of producing a rat exhibiting a rage reaction, comprising the steps of:

a) prenatally stimulating the $F_1$ generation by feeding the mother a tryptophan diet of about 3% during the third trimester of gestation;

b) inbreeding the $F_1$; and c) selecting $F_2$ exhibiting the rage reaction.

* * * * *

UNITED STATES PATENT AND TRADEMARK OFFICE
CERTIFICATE OF CORRECTION

PATENT NO. : 5,833,945

DATED : November 10, 1998     Page 1 of 3

INVENTOR(S) : Moto Sakuma

It is certified that error appears in the above-identified patent and that said Letters Patent is hereby corrected as shown below:

On the Title Page, under Related U.S. Application Data, line 2, after "1996" insert --(abandoned)--.

On the Title Page, under Related U.S. Application Data, line 3, after "1995" insert --(abandoned)--.

On the Title Page, under Related U.S. Application Data, line 4, after "1994" insert --(abandoned)--.

On the Title Page, under Related U.S. Application Data, line 5, after "1992" insert --(abandoned)--.

On the Title Page, under Other Publications, line 23, "Combnation" should be --Combination--.

On the Title Page, under Other Publications, line 25, "1:76" should be --1:78--.

On the Title Page, under Other Publications, line 35, "Quartlery" should be --Quarterly--

On the Title Page, under Other Publications, column 2, lines 7,8, "Hyerapobetalipoproteinemia" should be --Hyperapobetalipoproteinemia--.

On the Title Page, under Other Publications, column 2, line 8, "1980-188" should be --1980-1988--.

On the Title Page, under Other Publications, column 2, line 13, "Peack" should be --Peak--.

UNITED STATES PATENT AND TRADEMARK OFFICE
CERTIFICATE OF CORRECTION

PATENT NO. : 5,833,945
DATED : November 10, 1998
INVENTOR(S) : Moto Sakuma

Page 2 of 3

It is certified that error appears in the above-identified patent and that said Letters Patent is hereby corrected as shown below:

On the Title Page, under Other Publications, column 2, line 18, "Varous" should be --Various--.

On the Title Page, under Other Publications, column 2, lines 21,22, "Defferent" should be --Different--.

On the Title Page, under Other Publications, column 2, line 24, after "The" insert --α-Hydroxy Analogues of Isoleucine, Lysine, Threonine and Tryptophan And The--.

On the Title Page, under Other Publications, column 2, line 25, "Amno" should be --Amino--.

On Page 2 of the Title Page, under Other Publications, column 1, line 11, "Defiency" should be --Deficiency--.

On Page 2 of the Title Page, under Other Publications, column 1, line 15, "Defiency" should be --Deficiency--.

On Page 2 of the Title Page, under Other Publications, column 2, line 3, "Trytophan" should be --Tryptophan--.

Column 1, line 63, "SuppL" should be --Suppl.--.

Column 2, line 10, "Injection" should be --injection--.

Column 3, line 4, "Identified" should be --identified--.

UNITED STATES PATENT AND TRADEMARK OFFICE
CERTIFICATE OF CORRECTION

PATENT NO. : 5,833,945
DATED : November 10, 1998
INVENTOR(S) : Moto Sakuma

It is certified that error appears in the above-identified patent and that said Letters Patent is hereby corrected as shown below:

Column 4, line 36, after "generation" insert --.--

Column 4, line 36, after "." insert --The $F_0$ generation--.

Column 4, line 38, delete "parents ($F_1$) of these rats" and insert --control group ($F_0$)--.

Column 5, line 31, "Comer" should be --Corner--.

Column 6, line 24, insert --M > H--.

Column 7, line 3, "Implemented" should be --implemented--.

Column 8, line 1, delete "drawings,".

Signed and Sealed this

Twenty-fifth Day of May, 1999

Attest:

Q. TODD DICKINSON

*Attesting Officer*    *Acting Commissioner of Patents and Trademarks*